(12) United States Patent
Todd et al.

(10) Patent No.: US 8,834,574 B2
(45) Date of Patent: Sep. 16, 2014

(54) PROSTHETIC PATELLA

(75) Inventors: Dwight T. Todd, Columbia City, IN (US); Srinivas R. Setty, Bangalore (IN); Aravinda R. Bobba, Secunderabad (IN)

(73) Assignee: Zimmer, Inc., Warsaw, IN (US)

( * ) Notice: Subject to any disclaimer, the term of this patent is extended or adjusted under 35 U.S.C. 154(b) by 171 days.

(21) Appl. No.: 13/312,724

(22) Filed: Dec. 6, 2011

(65) Prior Publication Data

US 2012/0179264 A1 Jul. 12, 2012

Related U.S. Application Data

(60) Provisional application No. 61/420,537, filed on Dec. 7, 2010.

(51) Int. Cl.
*A61F 2/38* (2006.01)
*A61F 2/30* (2006.01)

(52) U.S. Cl.
CPC ..... *A61F 2/3877* (2013.01); *A61F 2002/30892* (2013.01); *A61F 2002/30822* (2013.01); *A61F 2002/30163* (2013.01); *A61F 2002/30878* (2013.01); *A61F 2002/30616* (2013.01)
USPC ...................................... 623/20.18

(58) Field of Classification Search
USPC ............................. 623/20.18–20.2
See application file for complete search history.

(56) References Cited

U.S. PATENT DOCUMENTS

| | | |
|---|---|---|
| 3,927,423 A | 12/1975 | Swanson |
| 4,944,756 A | 7/1990 | Kenna |
| 5,011,496 A | 4/1991 | Forte et al. |
| 5,133,758 A | 7/1992 | Hollister |
| 5,246,460 A | 9/1993 | Goodfellow et al. |
| 5,326,361 A | 7/1994 | Hollister |
| 5,507,820 A | 4/1996 | Pappas |
| 5,580,353 A | 12/1996 | Mendes et al. |
| 5,593,450 A | 1/1997 | Scott et al. |
| 5,609,640 A | 3/1997 | Johnson |
| 5,609,644 A | 3/1997 | Ashby et al. |
| 5,702,465 A | 12/1997 | Burkinshaw |

(Continued)

FOREIGN PATENT DOCUMENTS

| | | |
|---|---|---|
| CA | 2472669 A1 | 12/2005 |
| EP | 0613667 A1 | 9/1994 |

(Continued)

OTHER PUBLICATIONS

The partial search report/invitation to pay add'l fees mailed Mar. 7, 2012 in related International Application No. PCT/ US2011/063562.

(Continued)

*Primary Examiner* — Thomas J Sweet
*Assistant Examiner* — Megan Wolf
(74) *Attorney, Agent, or Firm* — Schwegman Lundberg & Woessner, P.A.

(57) ABSTRACT

A system of prosthetic patellar components including first and second prosthetic patellar components having dissimilar perimeter shapes and which are interchangeably usable without altering the securement feature formed on the natural patella or the position of the apex of the articulating surface of the prosthetic patella is described. A keyed securement feature as well as a patellar implant having a single offset mounting post for facilitating the proper placement of a patellar prosthesis on a natural patella based on patella tracking are also described.

17 Claims, 7 Drawing Sheets

(56) References Cited

U.S. PATENT DOCUMENTS

| | | |
|---|---|---|
| 5,723,016 A | 3/1998 | Minns et al. |
| 5,728,162 A | 3/1998 | Eckhoff |
| 5,824,099 A | 10/1998 | Mendes et al. |
| 5,871,539 A | 2/1999 | Pappas |
| 5,871,540 A | 2/1999 | Weissman et al. |
| 6,074,425 A | 6/2000 | Pappas |
| 6,616,696 B1 | 9/2003 | Merchant |
| 6,709,460 B2 | 3/2004 | Merchant |
| 6,802,864 B2 | 10/2004 | Tornier |
| 7,160,328 B2 * | 1/2007 | Rockwood et al. ........ 623/19.13 |
| 7,878,989 B2 | 2/2011 | McMinn |
| 2003/0120346 A1 | 6/2003 | Mercinek et al. |
| 2005/0143830 A1 | 6/2005 | Marcinek et al. |
| 2005/0165492 A1 | 7/2005 | Fritz |
| 2005/0222685 A1 | 10/2005 | Hayden et al. |
| 2005/0267584 A1 | 12/2005 | Burdulis, Jr. et al. |
| 2007/0021838 A1 * | 1/2007 | Dugas et al. ................. 623/20.3 |
| 2007/0100459 A1 | 5/2007 | Rhodes |
| 2007/0150066 A1 | 6/2007 | McMinn |
| 2007/0198022 A1 | 8/2007 | Lang et al. |
| 2008/0243258 A1 | 10/2008 | Sancheti |
| 2008/0281426 A1 | 11/2008 | Fitz et al. |
| 2008/0288080 A1 | 11/2008 | Sancheti |
| 2008/0300689 A1 | 12/2008 | McKinnon et al. |
| 2009/0036993 A1 | 2/2009 | Metzger |
| 2009/0222103 A1 | 9/2009 | Fitz et al. |
| 2009/0226068 A1 | 9/2009 | Fitz et al. |
| 2009/0326661 A1 | 12/2009 | Wright et al. |
| 2009/0326662 A1 | 12/2009 | Goldstein et al. |
| 2010/0125338 A1 | 5/2010 | Fitz |

FOREIGN PATENT DOCUMENTS

| | | |
|---|---|---|
| EP | 0613667 A1 | 9/1994 |
| EP | 0676182 A1 | 10/1995 |
| EP | 0681817 A1 | 11/1995 |
| EP | 0705580 A1 | 4/1996 |
| EP | 0728450 A2 | 8/1996 |
| EP | 0728450 B1 | 8/1996 |
| EP | 0736292 A2 | 10/1996 |
| EP | 1308142 A2 | 5/2003 |
| EP | 1308142 A2 | 5/2003 |
| EP | 1557144 A1 | 7/2005 |
| EP | 1557144 B1 | 7/2005 |
| EP | 1582184 A1 | 10/2005 |
| EP | 1582184 A1 | 10/2005 |
| EP | 1862150 A1 | 12/2007 |
| EP | 1862150 B1 | 12/2007 |
| EP | 2140836 A1 | 1/2010 |
| EP | 2140837 A1 | 1/2010 |
| EP | 2140837 A1 | 1/2010 |
| WO | WO90/14805 A1 | 12/1990 |
| WO | WO91/04715 A1 | 4/1991 |
| WO | WO92/03109 A1 | 3/1992 |
| WO | WO92/18069 A1 | 10/1992 |
| WO | WO93/00871 A1 | 1/1993 |
| WO | WO94/22396 A1 | 10/1994 |
| WO | WO94/22397 A1 | 10/1994 |
| WO | WO-95/14445 A1 | 6/1995 |
| WO | WO-97/25006 A1 | 7/1997 |
| WO | WO97/25006 A1 | 7/1997 |
| WO | WO97/42914 A1 | 11/1997 |
| WO | WO-97/42914 A1 | 11/1997 |
| WO | WO98/06343 A1 | 2/1998 |
| WO | WO01/70143 A1 | 9/2001 |
| WO | WO03/013338 A2 | 2/2003 |
| WO | WO-03/013338 A2 | 2/2003 |
| WO | WO-03/013339 A2 | 2/2003 |
| WO | WO03/013339 A2 | 2/2003 |
| WO | WO2004/110319 A1 | 12/2004 |
| WO | WO-2004/110319 A1 | 12/2004 |
| WO | WO2007/102951 A2 | 9/2007 |
| WO | WO2009/018365 A1 | 2/2009 |
| WO | WO-2009/018365 A1 | 2/2009 |
| WO | WO2009/111626 A2 | 9/2009 |

OTHER PUBLICATIONS

"International Application Serial No. PCT/US2011/063562, International Preliminary Report on Patentability mailed Jun. 20, 2013", 11 pgs.

"Patellar Component Medialization in Total Knee Arthroplasty", Aaron A. Hofmann, MD et al., The Journal of Arthroplasty vol. 12 No. 2, Feb. 1997, pp. 155-160.

"The Effect of Patellar Button Placement and Femoral Component Design on Patellar Tracking in Total Knee Arthroplasty", Ichiro Yoshii, MD et al., Clinical Orthopaedics and Related Research No. 275, Feb. 1992, pp. 211-219.

"The effect of component placement on knee kinetics after arthroplasty with an unconstrained prosthesis", M.C. Miller et al., Journal of Orthopaedic Research 19, 2001, pp. 614-620.

The International Search Report and Written Opinion mailed May 3, 2012 in related International Application No. PCT/US2011/063562.

Zimmer Natural-Knee II Primary System Surgical Technique, Zimmer Inc., 2004, 2005, 2009.

* cited by examiner

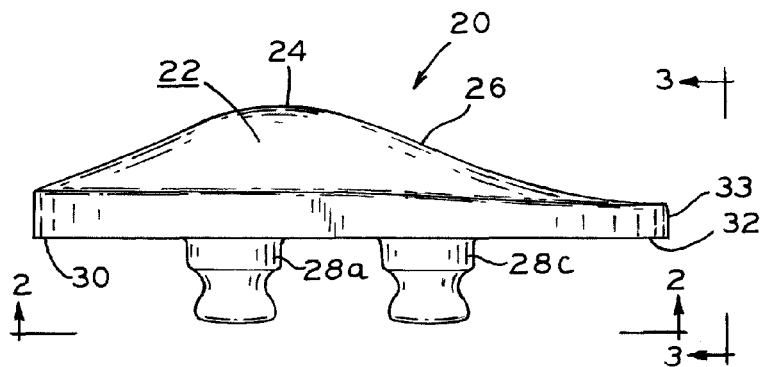
FIG_1
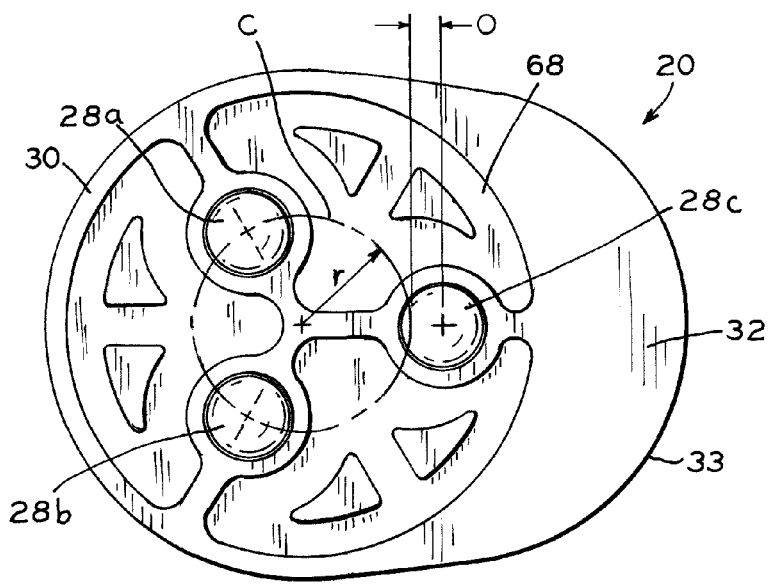
FIG_2
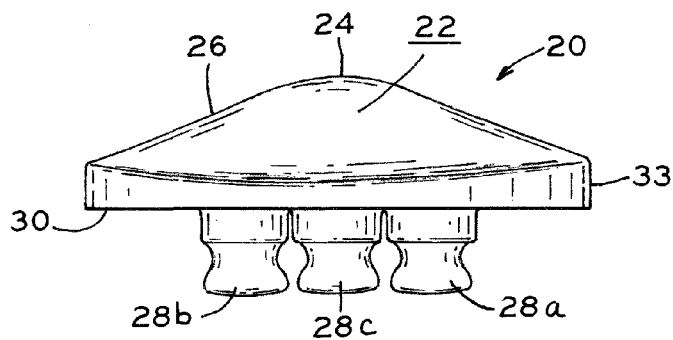
FIG_3

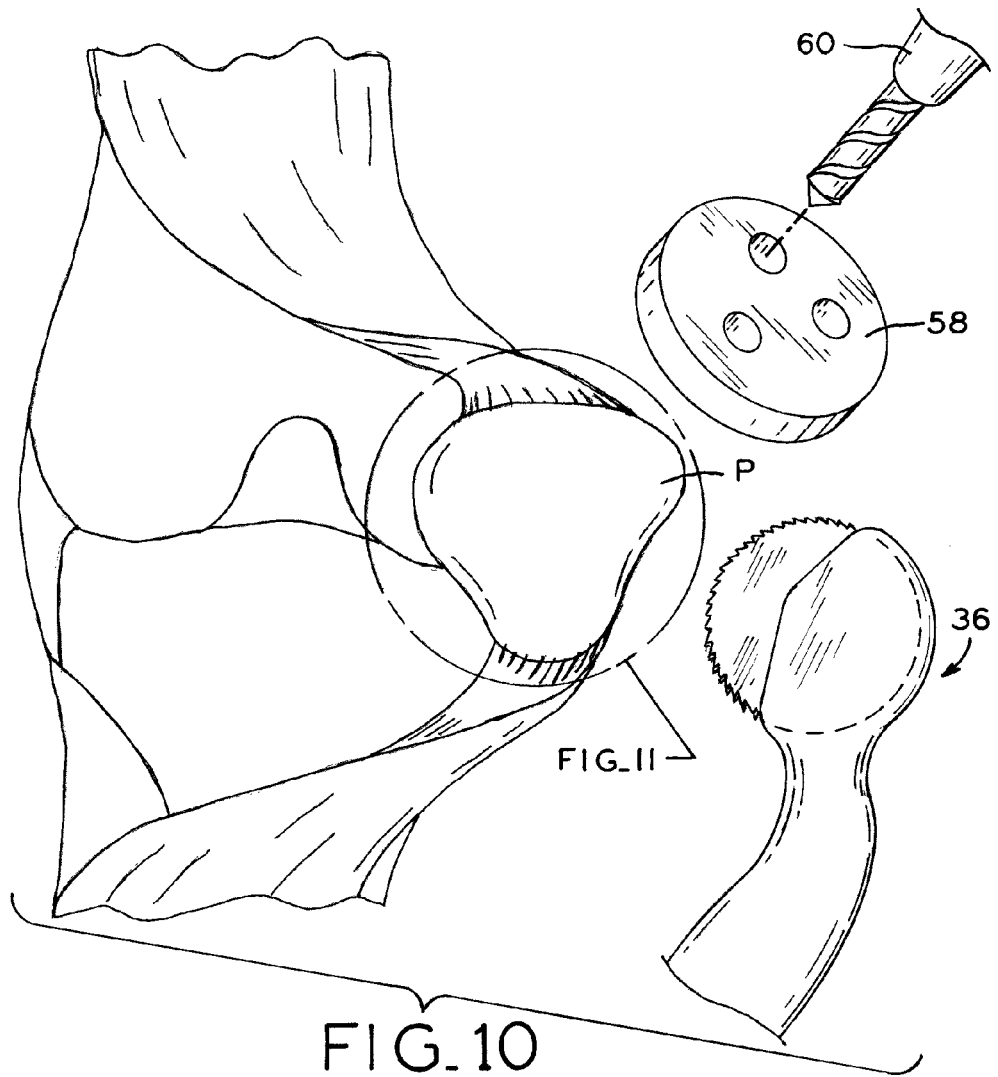
FIG_10
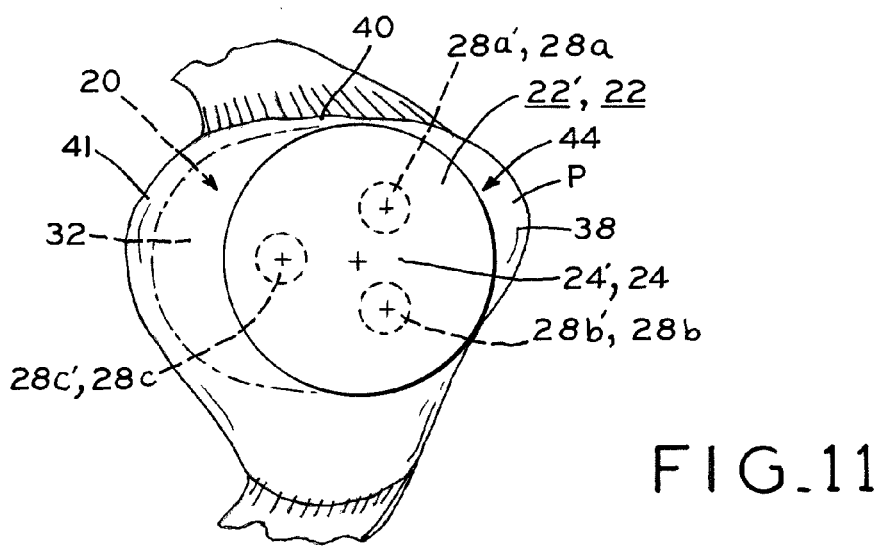
FIG_11

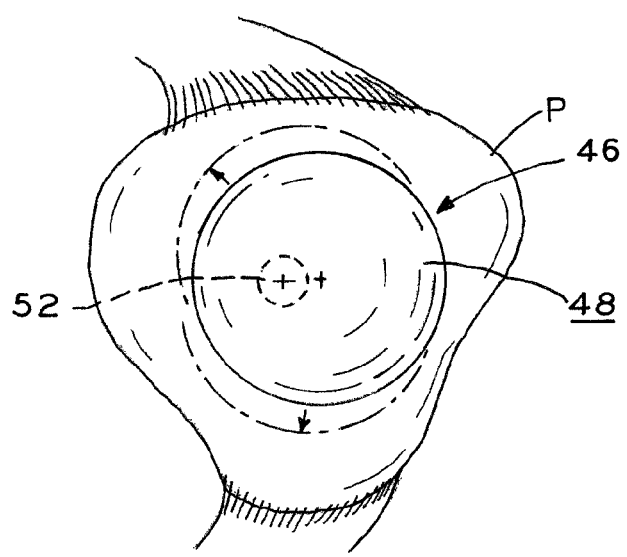
FIG_12
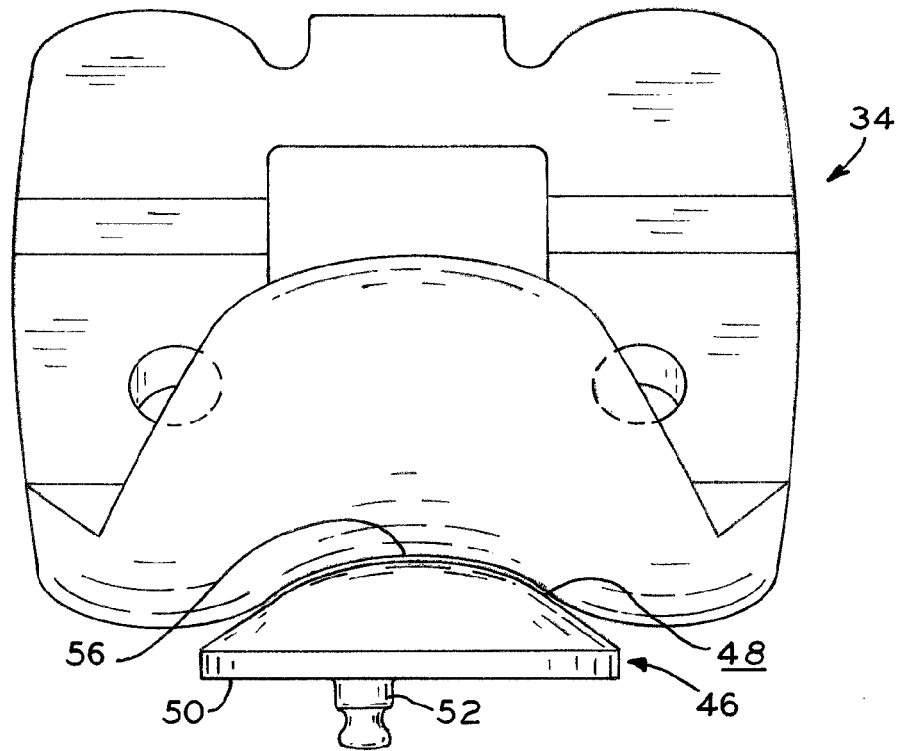
FIG_13

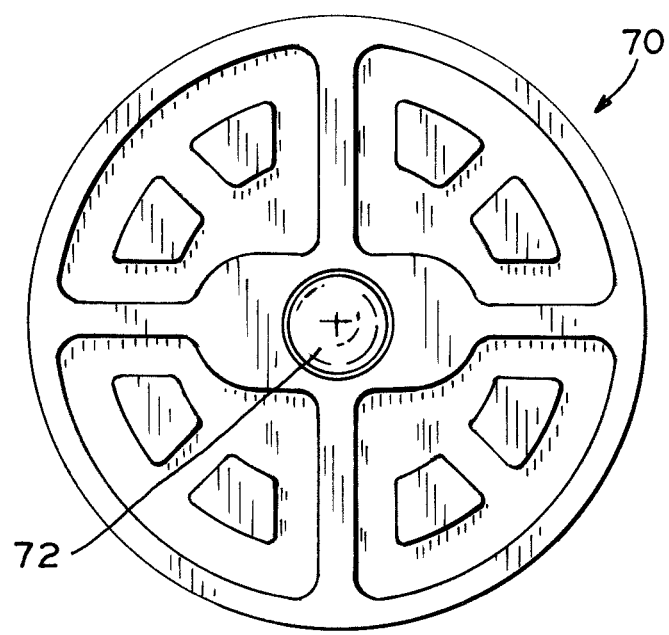
FIG_14

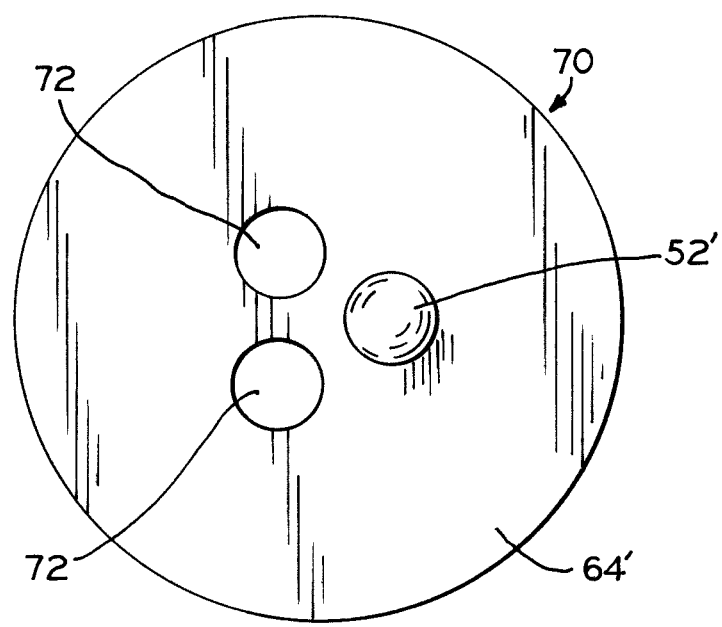
FIG_15

PROSTHETIC PATELLA

CROSS REFERENCE TO RELATED APPLICATIONS

This application is related to and claims the benefit under Title 35, U.S.C. 119(e) of U.S. Provisional Patent Application Ser. No. 61/420,537, entitled OFFSET PEG PATELLA, filed on Dec. 7, 2010, the entire disclosure of which is hereby expressly incorporated by reference herein.

BACKGROUND

The present disclosure relates to final and provisional implants used in knee arthroplasty, and, in particular, to final and provisional patellar implants for replacing a patellar articular surface and facilitating the proper placement of a patellar implant, respectively.

The knee joint is generally formed by the pair of condyles located at the distal portion of a femur, the tibial plateau located at the proximal end of a tibia and a pair of menisci positioned between the tibial plateau and the femoral condyles. The knee further includes the patella which is secured by the patellar tendon to ride against an anterior portion of the femur during articulation of the knee.

A knee may experience disease or trauma necessitating replacement of all or a portion of the knee with one or more prosthetic knee implants including prosthetic components such as a femoral component to replace the distal end of the femur, a tibial component to replace the proximal end of the tibia, a bearing insert to replace articulating tissue between the femur and the tibia and a patellar articular surface to replace the articulating surface of the patella. During replacement of the patellar articular surface, the patella may be everted to provide access to its posterior surface so that the posterior surface of the patella can be shaped to accommodate placement of a prosthetic patellar component thereon.

Knee prosthesis systems may include different sized femoral components, tibial components, bearing inserts and patellar articular surfaces. Patellar articular surfaces of differing sizes many times utilize differing securement mechanisms so that intraoperatively switching from one size to another necessitates altering the compatible securement features formed in the natural patella which receives the prosthetic patellar articular surface. In certain pre-existing systems, such as the Zimmer Natural Knee II System, a series of differently sized circular patellar prostheses may utilize compatible securement features so that the associated securement features formed in the natural patella do not have to be re-formed when intraoperatively choosing between two different size patellas. The patellas of this system all have a mathematically similar, i.e., circular perimeter shape. The Zimmer Natural Knee II System is shown and described in the Natural-Knee II Primary System Surgical Technique bearing copyright dates of 2004, 2005 and 2009, a copy of which is herewith submitted in an Information Disclosure Statement, the entire disclosure of which is hereby explicitly incorporated by reference herein.

SUMMARY

The present disclosure is, in one embodiment, directed to a system of prosthetic patellar components, i.e., patellar prostheses, including first and second prosthetic patellar components having dissimilar perimeter shapes and which are interchangeably usable without altering the securement feature formed on the natural patella. For the purposes of this document, "dissimilar" is used to describe the perimeter shapes of two patellar prostheses which are not 1) mathematically similar, i.e., exactly the same in shape but not necessarily size or 2) substantially mathematically similar, i.e., the same in shape within manufacturing tolerances but not necessarily size. In one embodiment, the first prosthetic patellar component includes a generally circular periphery while the second prosthetic patellar component includes a generally elongate periphery. In certain embodiments, the securement feature of the prosthetic patellar components incorporates a keying feature which allows for securement of the patellar prosthesis to the natural patella in only a single, desired position. The present disclosure is further directed to a provisional patellar implant for facilitating the proper placement of a final patellar implant on a natural patella. "Patellar prosthesis" and "prosthetic patellar component" are used interchangeably throughout this document. Both of these terms can denote either a final or a provisional patellar prosthesis.

In accordance with an aspect of the present disclosure, two patellar components having dissimilar perimeter shapes have identical securement features. For example, a non-circular, generally elongate patellar prosthesis of the present disclosure which is sized and shaped to provide substantial coverage of the superior aspect of the posterior surface of the natural patella includes a plurality of fixation posts extending from the bone contacting surface thereof to facilitate securement of the patellar prosthesis on the natural patella. The fixation posts of the non-circular, generally elongate patellar prosthesis of the present disclosure are sized the same as and arranged in an identical pattern with respect to a plurality of fixation posts extending from the bone contacting surface of a circular patellar prosthesis of the present disclosure so that the two prostheses are interchangeably usable with a natural patella without requiring modification of the attachment surface of the natural patella, i.e., without requiring redrilling of holes to accommodate the fixation posts.

Dissimilar patellar prostheses of the present disclosure further utilize a non-circular arrangement of fixation posts so that they are securable to the natural patella in only a single orientation. The non-circular orientation of the fixation posts is identical for each of the dissimilar prosthetic patellar components so that the dissimilar patellar prostheses are interchangeable as described above.

When implementing a method of replacing the articular surface of a patella in accordance with the present invention, a surgeon may first provide to the patient a first patellar prosthesis having a first patellar prosthesis perimeter shape, secure the first patellar prosthesis to the patella, evaluate the fit and coverage of the patellar prosthesis relative to the patella, thereafter provide a second patellar prosthesis having a second patellar prosthesis perimeter shape which is dissimilar from the first patellar prosthesis perimeter shape, secure the second patellar prosthesis to the patella without forming any additional patella securement features on the patella, evaluate the fit and coverage of the second patellar prosthesis relative to the patella and then choose one of the first patellar prosthesis and the second patellar prosthesis for final implantation based on the aforementioned evaluations. In practicing this method, the "first patellar prosthesis" and "second patellar prosthesis" may be either final or provisional patellar prostheses. Further, in the embodiments of the present invention, the first patellar prosthesis will be a symmetrical patellar prosthesis such as a circular patellar prosthesis, while the second patellar prosthesis will be an asymmetrical patellar prosthesis such as an elongate patellar prosthesis.

In a further aspect of the present disclosure, a trial patellar prosthesis includes a single fixation peg which is offset from the center of the patellar trial prosthesis. When using this trial prosthesis, a hole may be formed in the patella which is slightly larger than the single fixation post so that the trial patellar component may rotate about its fixation post during range of motion testing to allow the trial patellar prosthesis to automatically orient itself in a kinematically advantageous position relative to the natural patella. A set of final implants including a final implant which mirrors the trial patellar component, including its offset fixation peg, together with a final patellar implant having a central fixation peg may be utilized together with the aforementioned trial patellar prosthesis as further described hereinbelow.

The invention, in one form thereof, comprises a system of patellar prostheses including a first patellar prosthesis comprising a first patellar prosthesis perimeter defining a first patellar prosthesis perimeter shape and a first patellar prosthesis securement feature having a size and a shape; a second patellar prosthesis comprising a second patellar prosthesis perimeter defining a second patellar prosthesis perimeter shape, the second patellar prosthesis shape dissimilar from said first patellar prosthesis perimeter shape, and a second patellar prosthesis securement feature having the same size and shape as the first patellar prosthesis securement feature, whereby the first patellar prosthesis and the second patellar prosthesis are securable to a natural patella having a patella securement feature compatible with the size and shape shared by the first patellar prosthesis securement feature and the second patellar prosthesis securement feature to allow interchangeable securement of the first patellar prosthesis and the second patellar prosthesis to a natural patella.

The invention, in another form thereof, comprises a method of replacing the articular surface of a patella, including the steps of: providing a first patellar prosthesis comprising a first patellar prosthesis perimeter defining a first patellar prosthesis perimeter shape and a first patellar prosthesis securement feature having a size and a shape; forming a patella securement feature on the patella, the patella securement feature sized and shaped to cooperate with the first patellar prosthesis securement feature to secure the first patellar prosthesis to the patella; securing the first patellar prosthesis to the patella, using the first patellar prosthesis securement feature and the patella securement feature; removing the first patellar prosthesis from the patella; providing a second patellar prosthesis comprising a second patellar prosthesis perimeter defining a second patellar prosthesis perimeter shape, said second patellar prosthesis perimeter shape dissimilar from said first patellar prosthesis perimeter shape; a second patellar prosthesis securement feature having the size and shape of the first patellar prosthesis securement feature; and securing the second patellar prosthesis to the patella using a second patellar prosthesis securement feature and the patella securement feature.

The invention, in a further form thereof, comprises a patellar prosthesis including an articular surface, a base having a securement feature, the securement feature comprising a first fixation post having a first fixation post longitudinal axis intersecting said base at a first point, a second fixation post having a second fixation post longitudinal axis intersecting said base at a second point and a third fixation post having a third fixation post longitudinal axis intersecting said base at a third point, the first fixation post longitudinal axis and the second fixation post longitudinal axis arranged on a pitch circle of radius r, the third fixation post longitudinal axis offset from the pitch circle by a distance O, whereby said first point, said second point and said third point do not define an equilateral triangle.

The invention, in yet another form thereof, comprises a patellar prosthesis including an articular surface defining a dome sized to ride in a sulcus of one of a femur and a femoral and a femoral prosthesis, a bone contacting surface opposite the articular surface, and a securement feature comprising a single fixation post extending from the bone contacting surface, the bone contacting surface including a substantially planar bone contacting surface having no protrusions except for the securement feature extending therefrom, whereby, with the substantially planar bone contacting surface contacting the substantially planar osteotomized surface of a patella and the securement feature positioned in an aperture formed in the patella, the patellar prosthesis is rotatable relative to the patella, the single fixation post positioned such that the patellar prosthesis is rotatable relative to the patella to allow repositioning of the patellar prosthesis relative to the patella during range of motion testing to automatically reposition the patellar prosthesis to optimize patellar tracking during a fall range of motion of a knee joint including the patellar prosthesis.

The invention, in yet a further form thereof, comprises a method of positioning a patellar prosthesis on a patella of a knee joint, including the steps of: preparing a patella to receive a first patellar prosthesis, the step of preparing the patella to receive the first patellar prosthesis comprising the steps of osteotomizing the patella to form a substantially planar osteotomized surface of the patella and forming an aperture in the patella; providing a first patellar prosthesis comprising an articular surface defining a dome sized to ride in a sulcus of one of a femur and a femoral prosthesis, a bone contacting surface opposite the articular surface and a securement feature comprising single fixation post extending from the bone contacting surface, the bone contacting surface comprising a substantially planar bone contacting surface having no protrusions except for the securement feature extending therefrom, whereby, with the substantially planar bone contacting surface contacting the substantially planar osteotomized surface of the patella and the securement feature positioned in the aperture formed in the patella, the patellar prosthesis is rotatable relative to the patella, the single fixation post positioned such that the patellar prosthesis is rotatable relative to the patella to allow repositioning of the patella prosthesis relative to the patella during range of motion testing to automatically reposition the patellar prosthesis to optimize patellar tracking during a full range of motion of a knee joint including the patellar prosthesis; positioning the first patellar prosthesis fixation post in the aperture in the patella, the aperture sized to rotatably receive the first patellar prosthesis fixation post; positioning the substantially planar first patellar prosthesis bone contacting surface in contact with the substantially planar osteotomized surface of the patella; conducting a range of motion test of the knee, the first patellar prosthesis free to rotate relative to the patella during the range of motion test; determining a rotational position of the second patellar prosthesis relative to the patella for optimal patella tracking in the knee joint; and securing a final patellar prosthesis in the rotational position determined in the determining step.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is an elevational view of a non-circular, generally elongate patellar prosthesis of the present disclosure;

FIG. 2 is an elevational view illustrating the bone contacting surface of the patellar prosthesis of FIG. 1;

FIG. 3 is an alternate elevational view of the patellar prosthesis of FIG. 1;

FIG. 10 is an anterior view of a knee joint illustrating the patella in an everted position to allow for preparation of the posterior surface of the patella prior to placing a prosthetic patellar component thereon;

FIG. 11 is a detailed view of the patella illustrated in FIG. 10 showing placement of the patellar prosthesis of FIGS. 1-6 thereon and further schematically illustrating alternate placement of the patellar prosthesis of FIGS. 1-3 thereon;

FIG. 12 is an elevational view of the posterior surface of the patella of FIG. 10, showing placement of the trial patellar prosthesis of FIGS. 7-9 thereon;

FIG. 13 is an elevational view of a femoral prosthesis, with the patellar trial of FIGS. 7-9 positioned for articulation along the sulcus thereof;

FIG. 14 is an elevational view illustrating the bone contacting surface of a patellar prosthesis similar to the one illustrated in FIGS. 7-9, except that its mounting post is centrally located; and FIG. 15 is an elevational view of an alternative embodiment trial patellar prosthesis of the present invention which incorporates a fixation peg offset from the center of the trial prosthesis as well as a pair of drill guide holes used to form additional apertures in the native patella necessary to receive a plurality of mating fixation posts in the prosthetic patella.

Corresponding reference characters indicate corresponding parts throughout the several views. The exemplifications set out herein illustrate exemplary embodiments of the invention, and such exemplifications are not to be construed as limiting the scope of the invention in any manner.

DETAILED DESCRIPTION

Figure 4:
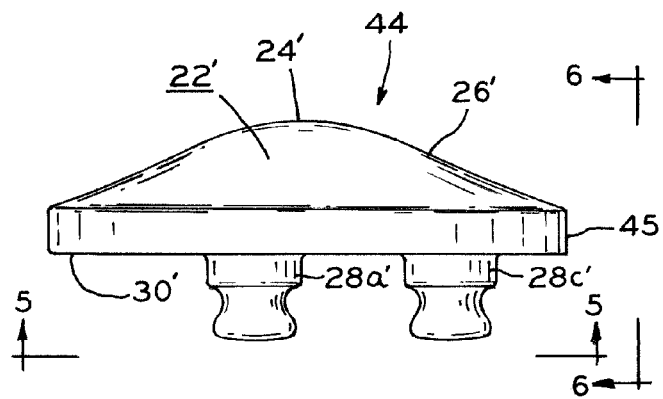
FIG. 4 is a radial elevational view of a second embodiment patellar prosthesis of the present disclosure which incorporates a substantially circular periphery.

Referring to FIGS. 1-3, elongate patellar prosthesis 20 includes articular surface 22 for articulating against the natural distal femur or a prosthetic distal femur such as femoral prosthesis 34 depicted in FIG. 13. Articular surface 22 includes domed portion 24 at an apex thereof. Domed portion 24 of articular surface 22 transitions into conical portion 26 of articular surface 22 toward base 30 of elongate patellar prosthesis 20. Extending from base 30 are fixation posts 28a, 28b and 28c. Fixation posts 28a-c can be utilized to secure elongate patellar prosthesis 20 to patella P (see, e.g., FIGS. 10 and 11) either alone, or in connection with a secondary securement mechanism such as bone cement.

To prepare patella P to receive elongate patellar prosthesis 20, an incision is made to expose the knee joint and patella P is everted as shown in FIG. 10. After everting patella P, bone cutting instrument 36 may be utilized to remove the posterior articular surface of patella P to form a substantially planar osteotomized surface of patella P. Thereafter, holes for receiving fixation posts 28a, 28b and 28c may be formed in the posterior surface of patella P. For example, template 58 may be positioned against the osteotomized posterior aspect of patella P to guide drill 60 to form a plurality of apertures corresponding in size and shape to fixation posts 28a, 28b and 28c. The apertures may be sized relative to fixation posts 28a, 28b and 28c so that an interference fit is formed between the natural patella and fixation posts 28a, 28b and 28c. The apertures may also be sized to receive bone cement to effect securement of patellar prosthesis 20 to patella P.

Elongate patellar prosthesis 20 of the present disclosure may be formed, e.g., of ultra high molecular weight polyethylene. Any of the patella prostheses of the present disclosure, including provisional patellar prostheses may be formed of biocompatible materials such as various polymers including ultra high molecular weight polyethylene, ceramic materials and metals such as stainless steel, titanium and cobalt chrome alloys. Further, any of the patellar prostheses including the provisional patella prostheses of the present disclosure may be formed in two piece configurations in which the articular surface is connected to a support member from which the fixations posts extend. The bone contacting side of a patellar prosthesis in accordance with the present invention may include bone ingrowth promoting material such as trabecular metal to facilitate securement of the patellar prosthesis to the patella.

Referring to FIG. 2, fixation posts 28a and 28b are positioned to extend from base 30 such that their longitudinal axes lie on a pitch circle C of radius r. As illustrated, in FIG. 2, fixation post 28c is offset front pitch circle C by offset distance O. In one exemplary embodiment, offset distance O equals 2 mm. Offset distance O can, in alternative embodiments, be as small as 1 mm, 1.5 mm or 2.0 mm, as large as 3 mm, 3.5 mm or 4 mm, or within any range defined by any pair of the foregoing values. In its broadest sense, offset distance O is any non zero distance. Not only is fixation post 28c offset from pitch circle C, but also the entire arrangement of fixation posts 28a, 28b and 28c are offset from the centroid of elongate patellar prosthesis 20. Stated another way, fixation posts 28a, 28b and 28c are not centrally located relative to elongate patellar prosthesis 20 either individually or as a group.

Placement of elongate patellar prosthesis 20 on prepared patella P is schematically illustrated in FIG. 11. Elongate patellar prosthesis 20 is positioned, in use, on patella P such that the apex of domed portion 24 of articular surface 22 is offset from a centroid of patella P in a direction toward medial aspect 38 and superior aspect 40 of patella P. As illustrated in FIGS. 1 and 2, elongate patellar prosthesis 20 includes base extension 32 which provides for an asymmetrical perimeter shape of elongate patellar prosthesis 20. Specifically, base extension 32 defines elongate perimeter 33. Generally, base extension 32 comprises a portion of base 30 which deviates from a circular base positioned beneath articular surface 22 of elongate patellar prosthesis 20. As illustrated in FIG. 11, base extension 32 occupies lateral aspect 41 of patella P such that elongate patellar prosthesis 20 significantly covers the prepared posterior surface of patella P.

Referring to FIGS. 1-3 and 11, the offset position of fixation post 28c relative to pitch circle C on which the longitudinal axes of fixation posts 28a and 28b are oriented creates a keying feature which dictates that elongate patellar prosthesis 20 can be secured to patella P in only the configuration illustrated in FIG. 11. To allow for fixation posts 28a, 28b and 28c to create the aforementioned keying feature, the longitudinal axes of fixation post 28a, 28b and 28c each intersect base 30 at a point, with the three points defining a triangle which is not an equilateral triangle. This keying feature is, of course, shared by template 58 (FIG. 10). Should elongate patellar prosthesis 20 be misoriented such that base extension 32 was rotated clockwise away from the orientation illustrated in FIG. 11, such that fixation post 28c was aligned with the aperture formed in patella P which was meant for fixation post 28b, then fixation posts 28a and 28b would be misaligned with the remaining holes formed in patella P and securement of elongate patellar prosthesis 20 to patella P would not be allowed. In this way, the offset of fixation post 28c from pitch circle C keys elongate patellar prosthesis 20 to patella P and eliminates the potential for malpositioning of elongate patellar prosthesis 20 with respect to patella P. Furthermore, the offset of the group of fixation posts 28a, 28b and 28c relative to the centroid of elongate patellar prosthesis 20 allows a surgeon to intraoperatively choose between elongate patellar prosthesis 20 and circular patellar prosthesis 44 (described in greater detail below) to provide best fit and coverage of the patella without being required to re-drill the peg holes or downsize the patella and without affecting the position of the apex of the dome (24) on the articulating side of the patella, and without affecting the position of the medial border of the patella implant with respect to the native patella.

Figure 5:
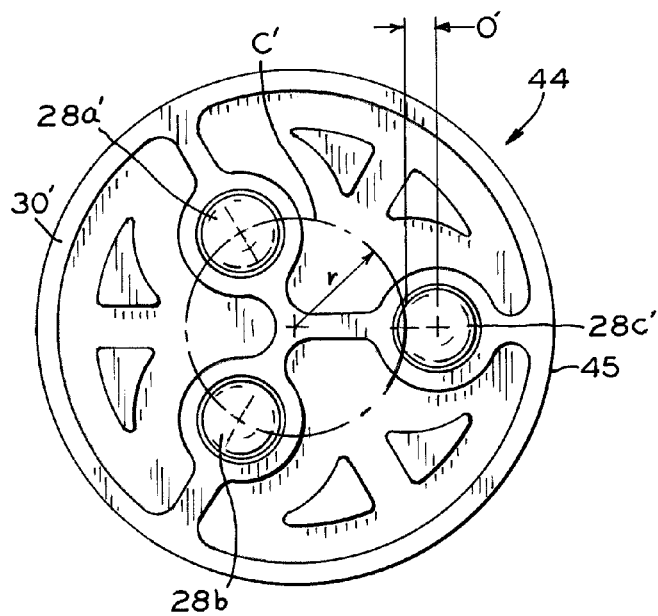
FIG. 5 is an elevational view illustrating the bone contacting surface of the patellar prosthesis of FIG. 4.
Figure 6:
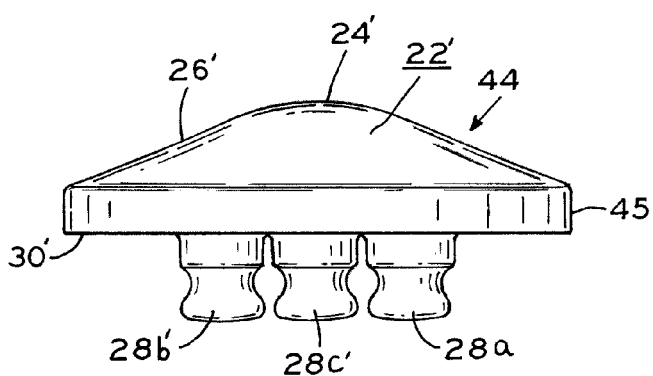
FIG. 6 is an alternate radial elevational view of the patellar prosthesis of FIG. 4.

Referring to FIGS. 4-6, circular patellar prosthesis 44 includes many of the same features as elongate patellar prosthesis 20. Identical parts which are shared between elongate patellar prosthesis 20 and circular patellar prosthesis 44 are denoted in the illustrations of patellar prosthesis 44 with primed reference numerals relative to the reference numerals associated with the drawings of elongate patellar prosthesis 20. Generally speaking, circular patellar prosthesis 44 is identical to elongate patellar prosthesis 20, but circular patellar prosthesis 44 excludes base extension 32. Therefore, circular patellar prosthesis 44 defines a symmetrical perimeter, specifically, circular perimeter 45. As with elongate patellar prosthesis 20, circular patellar prosthesis 44 includes fixation posts 28a' and 28b' having longitudinal axes positioned along pitch circle C'. As with elongate patellar prosthesis 20, circular patellar prosthesis 44 includes fixation post 28c' which is offset by a distance O' from pitch circle C'. Pitch circle C (FIG. 2) and pitch circle C' (FIG. 5) share an identical radius r, and distances O and O' are equal.

Because the configuration of fixation posts 28a', 28b' and 28c' of circular patellar prosthesis 44 is identical to the configuration of fixation posts 28a, 28b and 28c of elongate patellar prosthesis 20, a surgeon may intraoperatively decide to switch from elongate patellar prosthesis 20 to circular patellar prosthesis 44 or visa versa. Advantageously, positioning the group of fixation posts 28a, 28b and 28c such that they are offset relative to the centroid of elongate patellar prosthesis 20 allows for this interchangeability between elongate patellar prosthesis 20 and circular patellar prosthesis 44. Specifically, circular patellar prosthesis 44 of the present disclosure is generally implanted in a position that is medially and superiorly offset relative to the center of patella P, as illustrated in FIG. 11. If the group of fixation posts 28a, 28b and 28c of elongate patellar prosthesis 20 were centrally located with respect to elongate patellar prosthesis 20, proper positioning of circular patellar prosthesis 44 could not be accomplished without requiring the formation of a second set of holes to accommodate fixation posts 28a', 28b' and 28c' or potentially causing malpositioning of the patellar prosthesis such that the dome and the medial border of the patella prosthesis would shift from a desired position to an undesired position in which the medial border of the patella prosthesis might overhang the medial border of the native patella.

Figure 7:
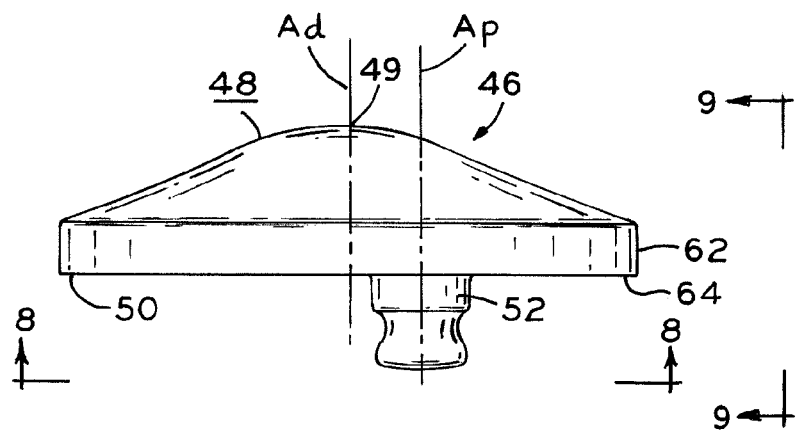
FIG. 7 is a radial elevational view of a trial patellar prosthesis of the present invention incorporating a fixation peg offset from the center of the trial prosthesis.
Figure 8:
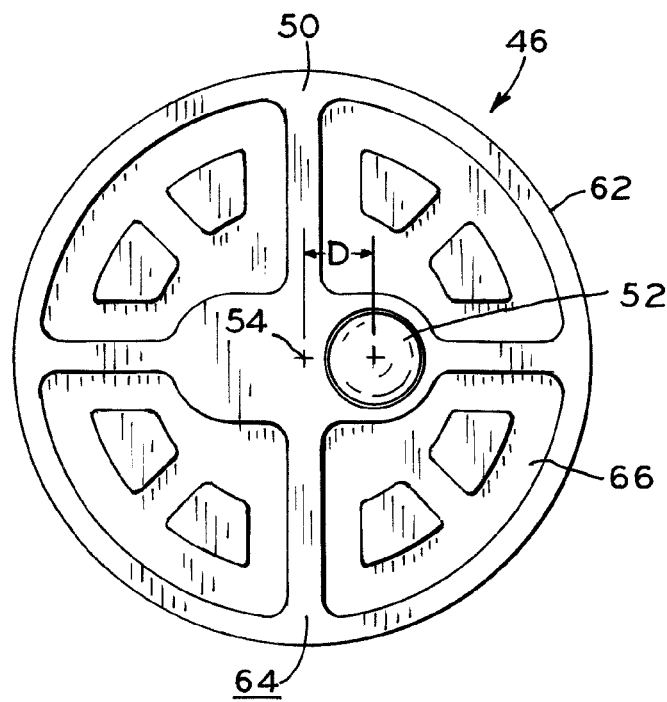
FIG. 8 is an elevational view illustrating the bone contacting surface of the patellar prosthesis of FIG. 7.
Figure 9:
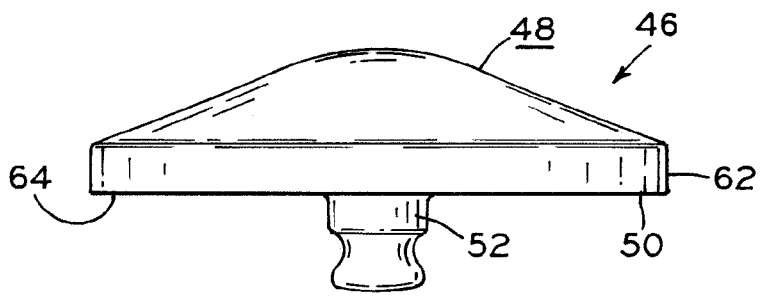
FIG. 9 is an alternate radial elevational view of the trial prosthesis of FIG. 7.

Referring to FIGS. 7-9, trial patellar prosthesis 46 includes articular surface 48, base 50 and mounting post 52. As illustrated in FIG. 8, mounting post 52 is offset from center 54 of trial patellar prosthesis 46 by a distance D. In one exemplary embodiment, offset distance D equals 2 mm. Offset distance D can, in alternative embodiments, be as small as 1 mm, 1.5 mm or 2 mm as large as 3 mm, 3.5 mm or 4 mm or within any range defined by any pair of the foregoing values. In its broadest sense, offset distance D is any nonzero distance. Trial patellar prosthesis 46 is substantially circular although trial patellar prosthesis 46 may take various shapes including one resembling that of elongate patellar prosthesis 20 described above. Trial patellar prosthesis 46 includes mounting post 52 which is eccentric, i.e., offset from the center of trial patellar prosthesis 46 to facilitate self orientation of trial patellar prosthesis 46 during range of motion testing, as will be further described hereinbelow. In certain embodiments, articular surface 48 includes domed portion 49 at an apex thereof, with domed portion 49 centrally located within circular prosthesis perimeter 62. In such an embodiment, longitudinal axis $A_d$ of domed portion 49 will be offset from longitudinal axis $A_p$ of mounting post 52 as illustrated in FIG. 7. In such embodiments, longitudinal axis $A_d$ is substantially coincident with center 54 (FIG. 8) of trial patellar prosthesis 46, with center 54 denoting the center of the bone contacting surface defined by base 50.

Referring to FIG. 2, a hole may be formed in patella P which is slightly oversized with respect to mounting post 52 of trial patellar prosthesis 46 to provide a clearance or slip fit with mounting post 52 of trial patellar prosthesis 46. Formation of such a hole may be effected by use of a template similar to template 58 illustrated in FIG. 10. Trial patellar prosthesis 46 may then be inserted with mounting post 52 positioned within the aforementioned hole in patella P. With this arrangement, trial patellar prosthesis 46 is free to rotate about the longitudinal axis of mounting post 52 and therefore to alter its rotational orientation with respect to patella P during range of motion testing. To allow for this relative rotation, base 50 of trial patellar prosthesis 46 defines substantially planar bone contacting surface 64 from which no protrusions except mounting post 52 extend. As illustrated in FIG. 8, bone contacting surface 64 may include indentations forming cement pockets 66 in which bone cement may reside in the case that trial patellar prosthesis 46 comprises a final patellar prosthesis as further described hereinbelow. Similar cement pockets can be utilized with any of the patellar prostheses in accordance with the present invention. For example, cement pockets 68 formed in elongate patellar prosthesis 20 are illustrated in FIG. 2. Referring to FIG. 13, trial patellar prosthesis 46 will ride in sulcus 56 of femoral prosthesis 34 (or the sulcus of a natural femur) during articulation of the knee. Such "patellar tracking", is optimized in accordance with this aspect of the present invention. During range of motion testing of the knee joint, trial patellar prosthesis 46 may rotate about the longitudinal axis of mounting post 52, as schematically illustrated in FIG. 12, until trial patellar prosthesis 46 has aligned itself in a kinematically favored position. Once this position of trial patellar prosthesis 46 is achieved, patella P may be marked to reflect the rotational orientation of trial patellar prosthesis 46 so that a final prosthesis may be similarly oriented. In an alternative embodiment of the present invention, trial patellar prosthesis 46 may include guide holes for forming apertures in patella P corresponding to fixation posts 28 of either elongate patellar prosthesis 20 or circular patellar prosthesis 44 described above.

This alternative embodiment is illustrated in FIG. 15. Parts shared between trial patellar prosthesis 70 illustrated in FIG. 15 and trial patellar prosthesis 46 illustrated in FIGS. 7-9 are indicated with primed reference numerals.

Referring to FIG. 15, trial patellar prosthesis 70 includes an articular surface which is not shown but is identical to articular surface 48 of trial patellar prosthesis 46. As illustrated in FIG. 15, mounting post 52' is offset from the center of trial patellar prosthesis 70. This offset mimics the offset of mounting post 52 of trial patellar prosthesis 46. Unlike patellar prosthesis 46 (FIGS. 7-9), trial patellar prosthesis 70 includes substantially planar bone contacting surface 64 but does not feature cement pockets 66. Substantially planar bone contacting surface 64' of trial patellar prosthesis 70 is planar, within manufacturing tolerances. In the event that patellar prosthesis 46 is a trial patellar prosthesis, it may include a planar bone contacting surface as described in conjunction with patellar prosthesis 70. Extending from substantially planar bone contacting surface 64' to the opposing articular surface (not shown) are guide holes 72. Guide holes 72 correspond to a pair of fixation posts extending from a corresponding final patellar prosthesis. In this way, guide hole 72 may be used to guide preparation of holes in a natural patella in a similar fashion to that described above with reference to FIG. 10. When using trial patellar prosthesis 70, the hole formed in the natural patella to accommodate mounting post 52' may be utilized in conjunction with holes formed through guide holes 72 to collectively provide a securement feature for a final patellar prosthesis.

In accordance with a further embodiment of the present disclosure, an implant may be constructed to mimic trial patellar prosthesis 46 illustrated in FIGS. 7-9. Specifically, the final prosthesis of this form of the present invention will have a mounting post which is offset from the center of the patellar prosthesis. In an alternative embodiment a final prosthesis 70 having centered peg 72 (FIG. 14) may also be provided. Including a set of single peg implants having a first implant with a centered mounting post and a second implant with an offset mounting post provides a surgeon with the flexibility to shift the position of the patella implant after drilling the peg hole. Specifically, the surgeon could use the patella implant with the centered peg but if he was not happy with the way the patella tracked during a range of motion trial during surgery, the surgeon could utilize trial patellar prosthesis 46 to determine, through a range of motion test, the optimal position for the patellar implant and thereafter implant the final patella implant with an offset peg in that same position. In the event that patellar prosthesis 46 comprises a final patellar prosthesis, cement pockets 66 may be utilized as a secondary securement feature together with mounting post 52 to effect final securement of patellar prosthesis 46 to patella P.

While this invention has been described as having exemplary designs, the present disclosure can be further modified within the spirit and scope of this invention. This application is therefore intended to cover any variations, uses, or adaptations of the invention using its general principles. Further, this application is intended to cover such departures from the present disclosure as come within known or customary practice in the art to which this invention pertains and which fall within the scope of the appended claims.

What is claimed is:

1. A system of patellar prostheses, comprising:
   a first patellar prosthesis comprising:
   a first patellar prosthesis perimeter defining a first patellar prosthesis perimeter shape; and
   a first patellar prosthesis securement feature having a size and a shape;
   a second patellar prosthesis comprising:
   a second patellar prosthesis perimeter defining a second patellar prosthesis perimeter shape, said second patellar prosthesis perimeter shape dissimilar from said first patellar prosthesis perimeter shape; and
   a second patellar prosthesis securement feature having said size and said shape, whereby said first patellar prosthesis and said second patellar prosthesis are securable to a natural patella having a patella securement feature compatible with said size and said shape shared by said first patellar prosthesis securement feature and said second patellar prosthesis securement feature to allow interchangeable securement of said first patellar prosthesis and said second patellar prosthesis to a natural patella, wherein the second patellar prosthesis securement feature includes a plurality of second prosthesis patellar fixation posts and the plurality of second prosthesis patellar fixation posts, as a group, are offset from a centroid of the second patellar prosthesis perimeter.

2. The system of patellar prosthesis of claim 1, wherein said first patellar prosthesis further comprises a first patellar prosthesis articular surface apex and said second patellar prosthesis further comprises a second patellar prosthesis articular surface apex, whereby with said first patellar prosthesis securement feature secured to the natural patella, said first patellar prosthesis articular surface apex maintains a first apex position relative to the natural patella and, with said second patellar prosthesis securement feature secured to the natural patella, said second patellar prosthesis articular surface apex maintains said first apex position relative to the natural patella.

3. The system of patellar prostheses of claim 1, wherein said first patellar prosthesis comprises a symmetrical patellar prosthesis and said first patellar prosthesis perimeter shape comprises a symmetrical perimeter shape, and wherein said second patellar prosthesis comprises an elongate patellar prosthesis and said second patellar prosthesis perimeter shape comprises an elongate perimeter shape.

4. The system of patellar prostheses of claim 3, wherein said first patellar prosthesis comprises a circular patellar prosthesis and said first patellar prosthesis perimeter shape comprises a circular perimeter shape.

5. The system of patellar prostheses of claim 1, wherein said first patellar prosthesis securement feature comprises a plurality of first patellar prosthesis fixation posts arranged in a pattern and wherein said second patellar prosthesis securement feature comprises the plurality of second prosthesis patellar fixation posts arranged in said pattern.

6. The system of prosthetic patellar components of claim 5, wherein said plurality of first patellar prosthesis fixation posts comprises:
   a first prosthetic fixation post having a first longitudinal axis;
   a second prosthetic fixation post having a second longitudinal axis; and
   a third prosthetic fixation post having a third longitudinal axis, said first longitudinal axis and said second longitudinal axis arranged on a pitch circle of radius r, said third longitudinal axis offset from said pitch circle by a distance O to form said pattern.

7. A patellar prosthesis, comprising:
   an articular surface;
   a base having a securement feature, said securement feature comprising:

a first fixation post having a first fixation post longitudinal axis intersecting said base at a first point;

a second fixation post having a second fixation post longitudinal axis intersecting said base at a second point; and a third fixation post having a third fixation post longitudinal axis intersecting said base at a third point, said first fixation post longitudinal axis and said second fixation post longitudinal axis arranged on a pitch circle of radius r, said third fixation post longitudinal axis offset from said pitch circle by a distance O, whereby said first point, said second point and said third point do not define an equilateral triangle, and the fixation posts of the securement feature, as a group, are offset from a centroid of the patellar prosthesis.

8. The patellar prosthesis of claim 7, wherein said distance O equals 2 mm.

9. The patellar prosthesis of claim 7, wherein said distance O comprises a distance in the range of 1-4 mm.

10. The patellar prosthesis of claim 7, wherein the patellar prosthesis further comprises an elongate patellar prosthesis perimeter.

11. The patellar prosthesis of claim 10, wherein said first, second and third fixation posts are offset from a centroid of the patellar prosthesis.

12. A patellar prosthesis, comprising:

an articular surface defining a dome sized to ride in a sulcus of one of a femur and a femoral prosthesis;

a bone contacting surface opposite said articular surface; and a securement feature comprising a single fixation post extending from said bone contacting surface, said bone contacting surface comprising a substantially planar bone contacting surface having no protrusions except for said securement feature extending therefrom, whereby, with said substantially planar bone contacting surface contacting a substantially planar osteotomized surface of a patella and said securement feature positioned in an aperture formed in the patella, the patellar prosthesis is rotatable relative to the patella, said single fixation post positioned such that the patellar prosthesis is rotatable relative to the patella to allow repositioning of the patellar prosthesis relative to the patella during range of motion testing to automatically reposition the patellar prosthesis to optimize patellar tracking during a full range of motion of a knee joint including the patellar prosthesis, wherein said single fixation post defines a fixation post longitudinal axis and said bone contacting surface has a center, said fixation post longitudinal axis offset from said center of said bone contacting surface.

13. The patellar prosthesis of claim 12, wherein the patellar prosthesis further comprises a circular patellar prosthesis perimeter.

14. The patellar prosthesis of claim 13, wherein said dome is centrally located within said circular patellar prosthesis perimeter.

15. The patellar prosthesis of claim 12, wherein said fixation post longitudinal axis is offset from a center of the patellar prosthesis.

16. The patellar prosthesis of claim 12, wherein said dome defines a dome longitudinal axis, said fixation post longitudinal axis offset from said dome longitudinal axis.

17. The patellar prosthesis of claim 16, wherein the patellar prosthesis further comprises a circular patellar prosthesis perimeter, and wherein said dome is centrally located within said circular patellar prosthesis perimeter.

* * * * *